United States Patent
Takahashi et al.

(10) Patent No.: US 6,685,970 B1
(45) Date of Patent: Feb. 3, 2004

(54) COMPOSITIONS CONTAINING PROANTHOCYANIDIN AND A VITAMIN $B_6$ DERIVATIVE OR A SALT THEREOF

(75) Inventors: Tomoya Takahashi, Ibaraki (JP); Asako Kobayashi, Ibaraki (JP); Chiemi Takaboshi, Ibaraki (JP); Minako Tajima, Ibaraki (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/657,614

(22) Filed: Sep. 8, 2000

(30) Foreign Application Priority Data

Sep. 21, 1999 (JP) ............................................. 11-266430

(51) Int. Cl.[7] ............................................... A61K 35/78
(52) U.S. Cl. ...................... 424/725; 424/777; 514/474; 514/400
(58) Field of Search ............................... 424/195.1, 581, 424/725, 777; 514/474, 400

(56) References Cited

U.S. PATENT DOCUMENTS

| | | | | |
|---|---|---|---|---|
| 4,698,360 A | * | 10/1987 | Masquelier | 514/456 |
| 5,536,506 A | * | 7/1996 | Majeed et al. | 424/464 |
| 5,569,458 A | * | 10/1996 | Grenberg | 424/195.1 |
| 5,804,594 A | * | 9/1998 | Murad | 514/474 |
| 5,939,076 A | * | 8/1999 | Allocca | 424/400 |
| 5,962,517 A | * | 10/1999 | Murad | 514/474 |
| 6,054,128 A | | 4/2000 | Wakat | |
| 6,126,940 A | * | 10/2000 | Takahashi et al. | 424/195.1 |

FOREIGN PATENT DOCUMENTS

| | | | |
|---|---|---|---|
| DE | 298 08 384 | 5/1998 | ............. A23L/2/02 |
| JP | 2166194 | 6/1990 | |
| JP | 5-112441 | 5/1993 | |
| JP | 5-163131 | 6/1993 | |
| JP | 8-2819 | 1/1996 | |
| JP | 9059154 | 3/1997 | |
| JP | 410007541 | * 1/1998 | |
| JP | 2744572 | 2/1998 | |
| JP | 11056299 | 3/1999 | |
| WO | WO 99/18814 | 4/1999 | |

OTHER PUBLICATIONS

Lubell A., (Jul. 1996) Cosmetic Dermatology vol. 9, No. 7, pp. 58–59.*
Ledbetter et al., J. Photochem. Photobiol. B: Biology 47(1): 12–21 (1998).*
"Purification of Apple Polyphenols and Characteristics of Components", Fragrance Journal, vol. 4 (1997), pp. 63–69 (with partial English translation).

* cited by examiner

*Primary Examiner*—Jean C. Witz
(74) *Attorney, Agent, or Firm*—Fitzpatrick, Cella, Harper & Scinto

(57) ABSTRACT

Proanthocyanidin-containing compositions with excellent proanthocyanidin stability, as well as drinks, foods, cosmetics and medicaments containing these compositions, are provided by admixing a vitamin $B_6$ derivative or its salt in proanthocyanidin. Also shown is a method for stabilizing proanthocyanidin to prevent its color change, etc. caused by oxidative polymerization and the like.

15 Claims, No Drawings

COMPOSITIONS CONTAINING PROANTHOCYANIDIN AND A VITAMIN $B_6$ DERIVATIVE OR A SALT THEREOF

FIELD OF THE INVENTION

This invention relates to compositions containing proanthocyanidin, drinks, foods, cosmetics and medicaments containing these compositions and a method for stabilizing proanthocyanidin.

BACKGROUND ART

It is known that proanthocyanidin, which is a substance contained in a number of plants and having a strong antioxidant effect, is susceptible to oxidation and quickly undergoes oxidative polymerization in the presence of oxygen, thereby showing a color change.

Conventional techniques to stabilize proanthocyanidin mainly include addition of potassium pyrosulfite (e.g., to wine) and addition of ascorbic acid (e.g., to apple juice).

JP-A-6-336420 discloses cosmetics containing sodium hydrogensulfite, 1-hydroxyethane-1,1-disulfonic acid, diethylenetriamine pentaacetic acid or phytic acid to prevent the color change of proanthocyanidin with the passage of time (the term "JP-A" as used herein means an "unexamined published Japanese patent application").

On the other hand, examples of methods for stabilizing polyphenol or preventing its color change or compositions for stabilizing polyphenol or preventing its color change are as follows: (1) a method for preventing the color change of polyphenol by adding a porphyrin zinc complex and an organic reducing agent to polyphenol as disclosed in JP-B-8-2819 (the term "JP-B" as used herein means an "examined Japanese patent publication"); (2) skin cosmetics containing a polyphenol compound together with a sucrose higher fatty acid ester disclosed in JP-A-5-112441; (3) skin cosmetics containing a polyphenol compound together with an alkyl glucoside disclosed in JP-A-5-163131; and (4) a method for preventing the color change of skin preparations for an external use which contain a polyphenol compound carrying at least 3 phenolic hydroxyl groups by adding a polyhydric alcohol or a sugar to the preparations disclosed in Japanese Patent No. 2,744,572.

SUMMARY OF THE INVENTION

An object of the invention is to provide proanthocyanidin-containing compositions having excellent proanthocyanidin stability, as well as drinks, foods, cosmetics and medicaments containing these compositions, and a method for stabilizing proanthocyanidin so as to prevent the color change, etc. caused by the oxidative polymerization, etc., thereof.

The invention provides compositions containing proanthocyanidin and a vitamin $B_6$ derivative or its salt, and drinks, foods, cosmetics and medicaments containing these compositions.

The invention further provides a method for stabilizing proanthocyanidin characterized by blending proanthocyanidin with a vitamin $B_6$ derivative or its salt.

The invention furthermore provides proanthocyanidin stabilizers containing a vitamin $B_6$ derivative or its salt.

DETAILED DESCRIPTION OF THE INVENTION

Particular examples of the vitamin $B_6$ derivative include pyridoxine, pyridoxal, pyridoxamine and phosphates thereof such as pyridoxal-5-phosphate. Pyridoxine, pyridoxal and pyridoxamine are compounds represented by the following general formula (I).

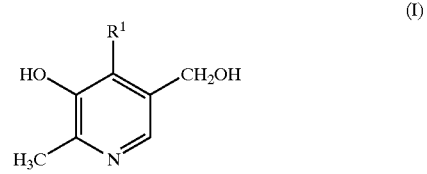

(I)

In the above formula, $R^1$ represents —$CH_2OH$ (pyridoxine), —CHO (pyridoxal), or —$CH_2NH_2$ (pyridoxamine).

Examples of the salt of the vitamin $B_6$ derivative include inorganic acid salts (hydrochloride, sulfate, nitrate, phosphate and the like) and organic acid salts (maleate, fumarate, citrate, acetate and the like) of the vitamin $B_6$ derivative, preferably dietary, cosmetically or pharmaceutically acceptable salts. The vitamin $B_6$ derivative or its salt may exist in the form of a hydrate or a solvate in some cases.

The vitamin $B_6$ derivative or its salt can be synthesized by a known method described in, for example, Kagaku-Daijiten (ed. by Kagaku-Daijiten Henshu Iinkai, vol. 7, p. 406, Aug. 5, 1962). Alternatively, a commercially available product may be employed.

Examples of proanthocyanidin include compounds having two or more flavan-7-ol derivatives, which are represented by the following general formula (II), bonded together.

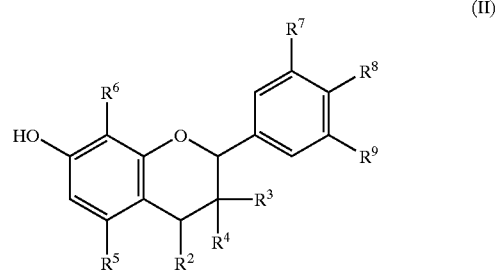

(II)

In the above formula, $R^3$ and $R^4$ are the same or different and each represents hydrogen, a hydroxyl group, a galloyloxy group or a glucopyranosyl group; and $R^2$, $R^5$, $R^6$, $R^7$, $R^8$ and $R^9$ are the same or different and each represents hydrogen or a hydroxyl group.

Preferable examples of the flavan-7-ol derivative represented by the general formula (II) include catechin, epicatechin, gallocatechin, epigallocatechin, afzelechin and epiaflezechin.

With respect to proanthocyanidin, a carbon atom of one flavan-7-ol derivative may be bonded to a carbon atom of another flavan-7-ol derivative through a single bond or an ether bond via an oxygen atom, etc. Any carbon or oxygen atom in formula (II) may participate in forming these bonds, although in the case of an ether bond, the bond is preferably formed via a hydroxyl group of the flavan-7-ol derivative. The flavan-7-ol derivatives which are bonded together to form proanthocyanidin may be either the same or different from each other.

The following general formulae (III-a), (III-b) and (III-c) show preferred examples of the bonding modes of these flavan-7-ol derivatives.

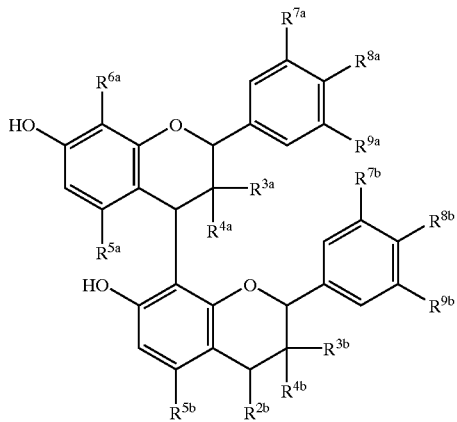

(III-a)

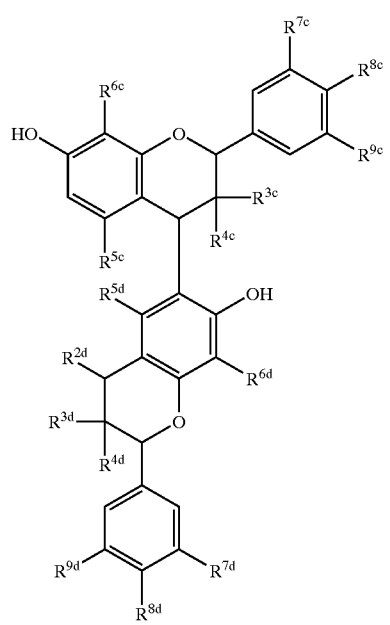

(III-b)

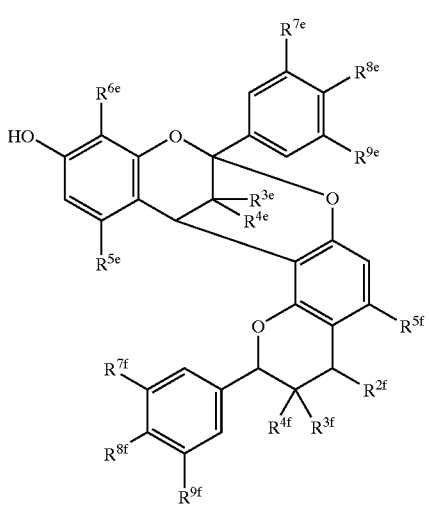

(III-c)

In the above formulae, $R^{3a}$, $R^{4a}$, $R^{3b}$, $R^{4b}$, $R^{3c}$, $R^{4c}$, $R^{3d}$, $R^{4d}$, $R^{3e}$, $R^{4e}$, $R^{3f}$, and $R^{4f}$, are the same or different and each represents hydrogen, a hydroxyl group, a galloyloxy group or a glucopyranosyloxy group; and $R^{5a}$, $R^{6a}$, $R^{7a}$, $R^{8a}$, $R^{9a}$, $R^{2b}$, $R^{5b}$, $R^{7b}$, $R^{8b}$, $R^{9b}$, $R^{5c}$, $R^{6c}$, $R^{7c}$, $R^{8c}$, $R^{9c}$, $R^{2d}$, $R^{5d}$, $R^{6d}$, $R^{7d}$, $R^{8d}$, $R^{9d}$, $R^{5e}$, $R^{6e}$, $R^{7e}$, $R^{8e}$, $R^{9e}$, $R^{2f}$, $R^{5f}$, $R^{7f}$, $R^{8f}$, and $R^{9f}$ are the same or different and each represents hydrogen or a hydroxyl group.

As the proanthocyanidin, it is preferable to use a compound having from 2 to 10, more preferably from 2 to 4, flavan-7-ol structural units as described above.

Examples of dimers of flavan-7-ol derivatives include epicatechin-catechin bonded compounds such as epicatechin-(4β→8)-catechin, epicatechin dimers such as epicatechin-(4β→6)-epicatechin and epicatechin-(β→8)-epicatechin (procyanidin B-2), and catechin-catechin dimers such as catechin-(4α→8)-catechin. Examples of trimers of flavan-7-ol derivatives include epicatechin trimers such as epicatechin-(4β→8)-epicatechin-(4β→8)-epicatechin and epicatechin-(4β→8)-epicatechin-(4β→6)-epicatechin, catechin trimers such as catechin-(4α→8)-catechin-(4α→8)-catechin, and mixed epicatechin-catechin trimers such as epicatechin-(4β→8)-epicatechin-(4β→8)-catechin.

In addition, compounds wherein gallic acid or sugars (glucose, rhamnose and the like) are bonded to the above-described compounds also fall within the concept of the proanthocyanidin as used in the invention.

Proanthocyanidin has various isomers including optical isomers and all of these isomers and mixtures thereof may be utilized in the present invention.

Proanthocyanidin can be obtained by extraction (and optional purification) from various plants such as a grape, an apple, a barley, a persimmon, a coconut, a cacao, a pine, a blueberry, a strawberry, an adzuki bean and a peanut, which belong to the genera Vitis, Malus, Hordeum, Diospyros, Cocos, Theobroma, Pinus, Vaccinium, Fragaria, Phaseolus, Arachis, etc. It is also possible to obtain proanthocyanidin optionally by purifying from fermented products of these extracts, such as a wine, a cider, a beer and the like.

The extraction and purification from a plant may be carried out in the following manner, which is known in the art (Chemical & Pharmaceutical Bulletin, 38: 3218, 1990 and ibid., 40: 889–898, 1992; Acta Derm. Venereol. (Stockh.), 78, 428 (1998) or the like).

A plant material (a fruit, a seed, a leaf, a stem, a root, a rhizome, etc.) is harvested at an appropriate time and then optionally dried by, for example, usual air-drying to give a material to be extracted. The starting material is ground or cut into pieces and then extracted by a solvent. As the extraction solvent, hydrophilic or lipophilic solvents such as water, alcohols (ethanol, methanol, isopropyl alcohol, etc.), ketones (acetone, methyl ethyl ketone, etc.), or esters (methyl acetate, ethyl acetate, etc.) may be used either alone or as a solvent mixture. The extraction temperature usually ranges from 0 to 100° C., preferably from 5 to 50° C.

The extraction is carried out for 1 hour to about 10 days. The solvent is used in an amount usually 1 to 30 times by weight, preferably 5 to 10 times by weight, based upon that of the dry material. The extraction may be carried out either under stirring or allowing to stand in an immersed state. The extraction procedure may be repeated twice or more, if necessary.

From the crude extract obtained above, insoluble residue is removed by filtration or centrifugation. Proanthocyanidin may be purified from the thus obtained extract, plant press juice or sap by well-understood methods known for separation and purification of crude drugs, preferably using biphasic solvent partition, column chromatography, preparative high-performance liquid chromatography, etc. either alone or in combination. The biphasic solvent partition can be carried out by, for example, extracting oily components and pigments from the above-mentioned extract with n-hexane, petroleum ether, etc. and eliminating the thus obtained extract, or by distributing the extract into a solvent (n-butanol, methyl ethyl ketone, etc.) and water and collecting proanthocyanidin from the solvent phase. The column chromatography method is exemplified by an ion exchange chromatography method with the use of Amberlite IR-120B, Amberlite IRA-402, etc. as a carrier, an adsorption column chromatography method with the use of normal phase silica gel, reversed phase silica gel, Diaion HP-20, Sepabeads SP-207, etc. as a carrier, and a gel filtration method with the use of Sephadex LH-20, etc. as a carrier. These can be used either alone or in combination repeatedly. Examples of the preparative high-performance liquid chromatography method include a reversed phase column chromatography method with the use of octadecyl silica, etc. and a normal phase column chromatography method with the use of silica gel, etc.

By the purification method as described above, water soluble ionic substances (salts, etc.), nonionic substances (saccharides, polysaccharides, etc.), oils, pigments, etc. are removed from the crude extract and thus proanthocyanidin is purified.

Proanthocyanidin originating in grape seeds can be obtained according to the method similar to that described in Acta Derm. Venereol. (stockh.), 78, 428 (1998).

As a method for producing proanthocyanidin by synthesis, Journal of the Chemical Society (Perkin Transaction I: 1535–1543, 1983) reports a method for producing an epicatechin or catechin dimer. Thus, various kinds of proanthocyanidin can be synthesized by the method reported in the above document or by the reference thereto.

An alcoholic fermentation product from a plant extract containing proanthocyanidin can be obtained by a known method as follows. In the case of a fermentative liquor of the simple fermentation type such as wine or cider, a fruit juice is subjected to alcoholic fermentation with the use of yeast. To produce a red wine from a grape juice, for example, grape fruits are ground and an antioxidant is added thereto. After adding 2 to 5% of yeast mash thereto, the main fermentation is carried out for 7 to 10 days. Next, the fermented liquor is pressed and the pericarp and the sediments are removed. Then the residue is transferred into a tapped barrel provided with a fermentation bung and subjected to after-fermentation at about 10° C. until the residual sugar content is reduced to 0.2% or less. After separating the sediments (tartar, tannin, protein, etc.), aging is continued for additional several years to give a wine product. In the case of a fermentative liquor of the multiple fermentation type such as beer, cereal starch employed as the starting material is first saccharified with amylase and then subjected to alcoholic fermentation. To produce beer by using barley as the major starting material, for example, wort is prepared from malt and water and then yeast is added thereto followed by fermentation. The main fermentation is carried out at 7 to 10° C. for 10 days. Then the fermented liquor is transferred into a storage tank and the after-fermentation is carried out at 0 to 2° C. for 60 days. After the completion of after-fermentation, the fermented liquor is filtered or sterilized under heating to give the desired fermentation product.

As a method for purifying proanthocyanidin from these alcoholic fermentation products, the methods discussed for crude extract, plant press juice or sap may be used so as to remove undesired water-soluble ionic substances (salts, etc.), nonionic substances (saccharides, polysaccharides, etc.), oils, pigments, etc.

When proanthocyanidin is used as a component in the composition according to the invention, proanthocyanidin of a single type or a mixture of two or more types may be used. Particular examples of the proanthocyanidin include grape seed extract proanthocyanidin, a purified red wine extract, proanthocyanidin originating in an apple, proanthocyanidin originating in a pine and purified proanthocyanidin oligomers.

The proanthocyanidin content in the composition of the invention may be determined depending on use, etc. without restriction. In the case of compositions to be used in drinks, foods, cosmetics, medicaments, etc., for example, the proanthocyanidin content ranges preferably from 0.01 to 20% by weight, more preferably form 0.1 to 10% by weight, based on the whole composition (the total weight of all of the components).

The content of the vitamin $B_6$ derivative or its salt in the composition of the invention may be determined depending on use, the type of proanthocyanidin, etc. without restriction. In the case of compositions to be used in drinks, foods, cosmetics, medicaments, etc., for example, the content ranges preferably from 0.001 to 1% by weight, more preferably form 0.005 to 0.5% by weight and further preferably from 0.01 to 0.3% by weight, based on the whole composition (the total weight of all of the components).

The composition of the invention may further contain antioxidants such as sodium hydrogensulfite, sodium pyrosulfite, ascorbic acid, erythorbic acid and tocopherols. Moreover, the composition of the invention may furthermore contain additives etc. appropriate for each of drinks, foods, cosmetics, medicaments, etc.

Now, drinks, foods, cosmetics and medicaments according to the invention each containing the composition of the invention will be described.

The drinks of the invention are desirably in the form of liquors such as fruit liquors, soft drinks, health drinks, tonic drinks, vitamin drinks, fruit drinks, etc.

The drinks of the invention can be obtained by adding the vitamin $B_6$ derivative or its salt to drinks containing proanthocyanidin, for example, (1) juices which are prepared by pressing plant materials and taken as such, e.g., fruit juices such as an apple juice, a grape juice and a blueberry juice; (2) drinks which are obtained by extracting from plant materials or processed products thereof with a hot water, e.g., various teas such as a barley tea, a green tea, an oolong tea, a black tea, a persimmon leaf tea and a Chinese matrimony vine tea; (3) drinks which are prepared by alcoholic fermentation of plant press juices, e.g., fruit liquors such as wine, cider and a blueberry liquor and alcoholic drinks such as beer and sparkling liquors; and (4) drinks which are prepared by immersing fruits in alcohol and extracting the extract, e.g., a Chinese quince liquor and a plum liquor. Soft drinks, health drinks and tonic drinks can also be produced by blending proanthocyanidin and the vitamin $B_6$ derivative or its salt optionally together with, for example, proteins, saccharides, fats, trace elements, vitamins, emulsifiers and perfumes and processing in the conventional manner.

The foods of the invention are in the form of tablets, capsules, powders, pills, jellies, frozen foods, powdery foods, sheet foods, bottled foods, canned foods, retort foods, etc. In addition, they may be processed into spontaneous liquid foods, half-digested nutritional foods, elemental nutritional foods and the like. The foods according to the invention preferably involve processed fruit products such as various jams and syruped fruits.

The foods of the invention can be produced by blending proanthocyanidin and the vitamin $B_6$ derivative or its salt with materials commonly employed in foods, for example, proteins, saccharides, fats, trace elements, vitamins, emulsifiers and perfumes and processing in the conventional manner.

The cosmetics of the invention may be in the form of liquids, gels, emulsions, solids such as creams, etc. Examples of the cosmetics according to the invention include lotions, cosmetic lotions, milky lotions, creams, packs, hair growth stimulant tonics and shampoos.

The cosmetics of the invention can be produced by blending proanthocyanidin and the vitamin $B_6$ derivative or its salt with materials commonly employed in cosmetics, for example, solid fats, semi-solid fats, liquid oils, humectants, emollients, surfactants, water-soluble polymers, fat-soluble polymers, organic or inorganic pigments, organic powders, UV absorbers, anti-inflammatory substances, refrigerants, preservatives, antioxidants, pH regulating agents (a citrate buffer solution, etc.), bactericides, vitamins, crude drugs and components thereof, skin softeners, perfumes, colorants, ethanol and purified water and processing in the conventional manner.

The medicaments of the invention are in the form of tablets, capsules, powders, pills, powders, fine powders, granules, syrups, troches, etc.

The medicaments of the invention can be produced by blending proanthocyanidin and the vitamin $B_6$ derivative or its salt optionally with other active ingredients of medicaments and processing in the conventional manner usually with the use of excipients. Examples of the excipients include saccharides (sorbitol, lactose, glucose, etc.), dextrin, starch, inorganic matters (calcium carbonate, calcium sulfate, etc.), a crystalline cellulose, a distilled water, a sesame oil, a corn oil, an olive oil and a cottonseed oil. Any excipient may be used so long as it is employed in general. To process into preparations, it is also possible to use additives such as binders, lubricants, dispersing agents, suspending agents, emulsifiers, diluents, buffers, antioxidants and bacteriostatic agents.

The compositions according to the invention and the drinks, foods, cosmetics and medicaments according to the invention containing these compositions are excellent in the stability of proanthocyanidin and suffer from little color change of proanthocyanidin with the passage of time.

The invention further provides a method for stabilizing proanthocyanidin characterized by blending proanthocyanidin with a vitamin $B_6$ derivative or its salt. This method can be carried out by setting various conditions including the content of the vitamin $B_6$ derivative or its salt as defined above with respect to the compositions of the invention and the drinks, foods, cosmetics and medicaments of the invention.

The invention furthermore provides proanthocyanidin stabilizers containing a vitamin $B_6$ derivative or its salt. Various conditions including the content of the vitamin $B_6$ derivative or its salt can be set as defined above with respect to the compositions of the invention and the drinks, foods, cosmetics and medicaments of the invention.

Now, various embodiments of the invention will be described in greater detail by reference to the following Examples, Test Examples and Reference Examples. In the following, (W/W) stands for (weight/weight), while (V/V) stands for (volume/volume).

EXAMPLE 1

The components as listed in the following Table 1 were mixed under stirring and solid matters were dissolved to give the compositions 1 to 5 according to the invention. Procyanidin B-2 was produced as shown in Reference Example 3.

TABLE 1

Compositions (% W/W) of compositions 1 to 5

| Component | Composition no. | | | | |
|---|---|---|---|---|---|
| | 1 | 2 | 3 | 4 | 5 |
| Pyridoxine hydrochloride | 0.1 | 0.3 | | | |
| Pyridoxamine | | | 0.01 | 0.03 | 0.06 |
| PB-2 | 1 | 1 | 1 | 1 | 1 |
| Citric acid | 0.25 | 0.25 | 0.25 | 0.25 | 0.25 |
| Sodium citrate | 0.25 | 0.25 | 0.25 | 0.25 | 0.25 |
| Ethanol | 70 | 70 | 70 | 70 | 70 |
| Purified water | 28.4 | 28.2 | 28.49 | 28.47 | 28.44 |

PB-2: procyanidin B-2 (the same will apply in the following tables)

EXAMPLE 2

The components as listed in the following Tables 2-1 and 2-2 were mixed under stirring and solid matters were dissolved to give the compositions 6 to 13 according to the invention. Procyanidin B-2 was produced as shown in Reference Example 3.

TABLE 2-1

Compositions (% W/W) of compositions 6 to 9

| Component | Composition no. | | | |
|---|---|---|---|---|
| | 6 | 7 | 8 | 9 |
| Pyridoxine hydrochloride | 0.03 | 0.06 | 0.1 | 0.3 |
| PB-2 | 1 | 1 | 1 | 1 |
| Citric acid | 0.25 | 0.25 | 0.25 | 0.25 |
| Sodium citrate | 0.25 | 0.25 | 0.25 | 0.25 |
| Sodium hydrogensulfite | 0.05 | 0.05 | 0.05 | 0.05 |
| Ethanol | 70 | 70 | 70 | 70 |
| Purified water | 28.42 | 28.39 | 28.35 | 28.15 |

TABLE 2-2

Compositions (% W/W) of compositions 10 to 13

| Component | Composition no. | | | |
|---|---|---|---|---|
| | 10 | 11 | 12 | 13 |
| Pyridoxal hydrochloride | 0.01 | 0.03 | 0.06 | 0.1 |
| PB-2 | 1 | 1 | 1 | 1 |
| Citric acid | 0.25 | 0.25 | 0.25 | 0.25 |
| Sodium citrate | 0.25 | 0.25 | 0.25 | 0.25 |
| Sodium hydrogensulfite | 0.05 | 0.05 | 0.05 | 0.05 |
| Ethanol | 70 | 70 | 70 | 70 |
| Purified water | 28.44 | 28.42 | 28.39 | 28.35 |

EXAMPLE 3

The components as listed in the following Tables 3-1 and 3-2 were mixed under stirring and solid matters were dissolved to give the compositions 14 to 18 according to the invention. Procyanidin B-2 was produced as shown in Reference Example 3.

TABLE 3-1

Compositions (% W/W) of compositions 14 to 16

| Component | Composition no. 14 | 15 | 16 |
|---|---|---|---|
| Pyridoxine hydrochloride | 0.06 | 0.1 | 0.3 |
| PB-2 | 1 | 1 | 1 |
| Citric acid | 0.25 | 0.25 | 0.25 |
| Sodium citrate | 0.25 | 0.25 | 0.25 |
| Purified water | 98.44 | 98.4 | 98.3 |

TABLE 3-2

Compositions (% W/W) of compositions 17 and 18

| Component | Composition no. 17 | 18 |
|---|---|---|
| Pyridoxamine hydrochloride | 0.1 | 0.3 |
| PB-2 | 1 | 1 |
| Citric acid | 0.25 | 0.25 |
| Sodium citrate | 0.25 | 0.25 |
| Purified water | 98.4 | 98.3 |

EXAMPLE 4

The components as listed in the following Table 4 were mixed under stirring and solid matters were dissolved to give the compositions 19 to 23 according to the invention. Procyanidin B-2 was produced as shown in Reference Example 3.

TABLE 4

Compositions (% W/W) of compositions 19 to 23

| Component | 19 | 20 | 21 | 22 | 23 |
|---|---|---|---|---|---|
| Pyridoxine hydrochloride | 0.01 | 0.03 | 0.06 | 0.1 | 0.3 |
| PB-2 | 1 | 1 | 1 | 1 | 1 |
| Citric acid | 0.25 | 0.25 | 0.25 | 0.25 | 0.25 |
| Sodium citrate | 0.25 | 0.25 | 0.25 | 0.25 | 0.25 |
| Sodium hydrogensulfite | 0.05 | 0.05 | 0.05 | 0.05 | 0.05 |
| Purified water | 98.44 | 98.42 | 98.39 | 98.35 | 98.15 |

EXAMPLE 5

Production of an Apple Juice

Pyridoxine hydrochloride (10 g) was added to 100 kg of a cloudy apple juice obtained in Reference Example 1 to give an apple juice bulk. Then it was filled into a paper pack container to give the final product.

EXAMPLE 6

Production of a Wine

Pyridoxine hydrochloride (10 g) was added to 100 kg of a fermented grape liquor stored in a barrel obtained in Reference Example 2 and dissolved therein by homogeneously stirring to a product. Then it was filled into a glass container to give the final product.

EXAMPLE 7

Production of a blueberry jam

| a blueberry | 100 kg |
|---|---|
| granulated sugar | 60 kg |
| a lemon juice | 1 kg |
| pyridoxine hydrochloride | 0.03 kg. |

(Preparation Method)

Granulated sugar was added to washed blueberries and the mixture was heated for 30 minutes. After cooling, a lemon juice and pyridoxine hydrochloride were added thereto and mixed therewith homogeneously. Then the mixture was filled in a glass container to give the final product.

EXAMPLE 8

Preparation of drink (a health drink)

| Proanthocyanidin originating in grape seeds (Reference Example 4) | 1.0 g |
|---|---|
| pyridoxine hydrochloride | 0.1 g |
| sodium benzoate | 1.0 g |
| fructose | 10.0 g |
| a perfume (fruit mix) | q.s. |
| a colorant (a blueberry colorant) | q.s. |
| a purified water | q.s. |
| total | 1000 g. |

(Preparation Method)

The above mixture was dissolved by homogeneously stirring, filled into a bottle and heated to give the final product.

EXAMPLE 9

Preparation of a lotion

| (An oily phase component) | |
|---|---|
| a perfume (menthol) | 0.05 g |
| a polyoxyethylene (60 mol) hardened castor oil (manufactured by Nippon Emulsion K.K.) | 2.0 g |
| 1,3-butylene glycol | 5.0 g |
| (An aqueous phase component) | |
| procyanidin B-2 (Ref. Ex. 3) | 0.5 g |
| pyridoxine hydrochloride | 0.06 g |
| glycerol | 5.0 g |
| methylparaben | 0.1 g |
| citric acid | 0.1 g |
| sodium citrate | 0.2 g |
| ethanol | 8.0 g |
| a purified water | q. s. |
| total weight of oily phase and aqueous phase components | 100.0 g. |

(Preparation Method)

The oily phase components and the aqueous phase components were each homogeneously dissolved. Then the oily phase was added to the aqueous phase under stirring to give a lotion.

EXAMPLE 10

| Preparation of a milky lotion | |
|---|---|
| (An oily phase component) | |
| squalane | 4.0 g |
| a wheat germ Oil | 2.0 g |
| monoglyceryl stearate | 1.0 g |
| polyoxyethylene stearyl ether (manufactured by Nippon Emulsion K.K.) | 4.0 g |
| propylparaben | 0.1 g |
| (An aqueous phase component) | |
| procyanidin B-2 (Ref. Ex. 3) | 0.5 g |
| pyridoxine hydrochloride | 0.06 g |
| methylparaben | 0.1 g |
| propylene glycol | 0.1 g |
| polyethylene glycol 6000 (manufactured by Nippon Oil and Fats Co., Ltd.) | 0.2 g |
| 1% sodium hyaluronate | 5.0 g |
| a purified water | q.s. |
| total weight of oily phase and aqueous phase components | 100.0 g. |

(Preparation Method)

The oily phase components and the aqueous phase components were each homogenized by heating to 80° C. and then the aqueous phase was added to the oily phase under stirring to give a milky lotion.

EXAMPLE 11

| Preparation of a hair tonic | |
|---|---|
| (An oily phase component) | |
| ethanol | 70 g |
| dl-α-tocopherol acetate | 0.2 g |
| pantothenyl alcohol | 0.3 g |
| a polyoxyethylene (60 mol) hardened castor oil (manufactured by Nippon Emulsion K.K.) | 1.0 g |
| propylene glycol | 3.0 g |
| a perfume (menthol) | trace |
| (An aqueous phase component) | |
| procyanidin B-2 (Ref. Ex. 3) | 1.0 g |
| pyridoxine hydrochloride | 0.06 g |
| biotin | 0.0001 g |
| a swertia japonica extract | 3.0 g |
| citric acid | 0.04 g |
| sodium citrate | 0.03 g |
| sodium hydrogensulfite | 0.1 g |
| a purified water | q.s. |
| total weight of oily phase and aqueous phase components | 100.0 g. |

(Preparation Method)

The oily phase components and the aqueous phase components were each homogenized at room temperature and then the aqueous phase was added to the oily phase under stirring to give a hair tonic.

EXAMPLE 12

| Preparation of tablets | |
|---|---|
| Proanthocyanidin originating in grape seeds (Reference Example 4) | 10.0 g |
| pyridoxine hydrochloride | 1.0 g |
| lactose | 89.0 g |
| a dry corn starch | 2.0 g |
| a talc | 1.8 g |
| calcium stearate | 0.2 g |

(Preparation Method)

These components were homogeneously mixed and the mixture was shaped into tablets (diameter: 7 mm, weight: 250 mg) with the use of a single-tabletting machine.

EXAMPLE 13

| Preparation of a vitamin drink | |
|---|---|
| Proanthocyanidin originating in grape seeds (Reference Example 4) | 0.3 g |
| pyridoxine hydrochloride | 0.03 g |
| taurine | 1.0 g |
| thiamine | 0.001 g |
| an Eleutherococcus extract (manufactured by Morinaga Milk Industry Co., Ltd.) | 0.004 g |
| ascorbic acid | 0.1 g |
| citric acid | 0.5 g |
| a fructose/glucose liquid sugar (F-55: (manufactured by Sanmatsu Kogyo K.K.) | 20 g |
| sodium benzoate | 0.04 g |
| a perfume (fruit mix) | q.s. |
| a purified water | q.s. |
| total | 100.0 g. |

(Preparation Method)

These components were homogeneously dissolved by stirring and filled in a glass container. After heating, the final product was obtained.

TEST EXAMPLE 1

Measurement of Color Change of Proanthocyanidin with the Passage of Time

The compositions 1 to 22 obtained in Examples 1 to 4 were stored at 50° C. for 1 week or 4 weeks. Then, the absorbance was measured at a wavelength of 400 nm (optical path length: 1 cm) in cases of the compositions 1 to 9 and 14 to 22 and compositions of the control groups corresponding thereto, and at a wavelength of 500 nm (optical path length: 1 cm) in cases of the compositions 10 to 13 and compositions of the control groups corresponding thereto. The compositions of the control groups were prepared each by using the same components as the corresponding composition except that the vitamin $B_6$ derivative or its salt was removed.

Tables 5 to 8 show the results.

TABLE 5

Color change after storing at 50° C. for 1 week
(a 70% (W/W) aqueous solution of ethanol)

| Sample | Absorbance |
| --- | --- |
| Control (Compositions 1 and 2) | 0.499 |
| Composition 1 | 0.426 |
| Composition 2 | 0.439 |
| Control (Compositions 3 to 5) | 0.472 |
| Composition 3 | 0.405 |
| Composition 4 | 0.393 |
| Composition 5 | 0.409 |

TABLE 6

Color change after storing at 50° C. for 1 week
(a 70% (W/W) aqueous solution of ethanol)

| Sample | Absorbance |
| --- | --- |
| Control (Compositions 6 to 9) | 0.519 |
| Composition 6 | 0.315 |
| Composition 7 | 0.21 |
| Composition 8 | 0.123 |
| Composition 9 | 0.104 |
| Control (Compositions 10 to 13) | 0.198 |
| Composition 10 | 0.136 |
| Composition 11 | 0.098 |
| Composition 12 | 0.083 |
| Composition 13 | 0.112 |

TABLE 7

Color change after storing at 50° C. for 4 weeks
(an aqueous solution)

| Sample | Absorbance |
| --- | --- |
| Control (Compositions 14 to 16) | 3.08 |
| Composition 14 | 2.108 |
| Composition 15 | 2.111 |
| Composition 16 | 2.663 |
| Control (Compositions 17 and 18) | 0.561 |
| Composition 17 | 0.498 |
| Composition 18 | 0.472 |

TABLE 8

Color change after storing at 50° C. for 4 weeks
(an aqueous solution)

| Sample | Absorbance |
| --- | --- |
| Control (Compositions 19 to 22) | 0.172 |
| Composition 19 | 0.119 |
| Composition 20 | 0.104 |
| Composition 21 | 0.144 |
| Composition 22 | 0.145 |

These results indicate that the compositions according to the invention show only a little color changes of proanthocyanidin with the passage of time, compared with the compositions of the control groups.

TEST EXAMPLE 2

Proanthocyanidin Stability Test

The compositions 6 to 8 obtained in Example 2, the compositions 14 and 15 obtained in Example 3, the compositions 19 to 23 obtained in Example 4 and the corresponding compositions of the control groups were stored at 50° C. for 2 or 4 weeks. Then the procyanidin B-2 content was measured by high-performance liquid chromatography (HPLC) under the analytical conditions as defined below. The compositions of the control groups were prepared each by using the same components as the corresponding composition except that the vitamin $B_6$ derivative or its salt was omitted.

(Analytical Conditions for HPLC)

Column: Inertsil ODS-2 manufactured by GL Science (diameter: 4.6 mm, length: 250 mm)
Mobile phase: acetonitrile/0.05% trifluoroacetic acid (volume ratio: 9/91)
Detector: UV 280 nm.

The procyanidin B-2 retention ratios given in the table were calculated in accordance with the following equation.

Procyanidin B-2 retention ratio=A/B×100 (%)

A: procyanidin B-2 content before test
B: procyanidin B-2 content after 2 or 4 weeks Tables 9 and 10 show the results of Test Example 2.

TABLE 9

Procyanidin B-2 retention ratio after
storing at 50° C. for 2 weeks
(a 70% (W/W) aqueous solution of ethanol)

| Sample | Retention ratio (%) |
| --- | --- |
| Control (Compositions 6 to 8) | 84.3 |
| Composition 6 | 87.9 |
| Composition 7 | 88.2 |
| Composition 8 | 88.7 |

TABLE 10

Procyanidin B-2 retention ratio after
storing at 50° C. for 4 weeks
(an aqueous solution)

| Sample | Retention ratio (%) |
| --- | --- |
| Control (Compositions 14 to 15) | 78.4 |
| Composition 14 | 83.6 |
| Composition 15 | 83.5 |
| Control (Compositions 19 to 23) | 79.7 |
| Composition 19 | 88.3 |
| Composition 20 | 89.2 |
| Composition 21 | 88.4 |
| Composition 22 | 87.5 |
| Composition 23 | 86.0 |

These results indicate that the compositions according to the invention are superior in the proanthocyanidin stability to the compositions of the control groups.

Reference Example 1

Production of a Cloudy Apple Juice

Washed apples (1 t, species: Fuji) were ground with a grinder and 10 kg of a 10% aqueous solution of ascorbic acid was added thereto. Next, the mixture was pressed and then filtered through a 60-mesh sieve. Subsequently, it was sterilized at 95° C. for 20 seconds with the use of an instantaneous sterilizer and immediately cooled. After centrifuging, a cloudy apple juice was obtained.

Reference Example 2

Production of a Fermented Grape Liquor Stored in a Barrel

Grapes (10 t, *Cabernet sauvignon*) were ground with a grinder and 800 g of potassium pyrosulfite was added thereto. After adding 3% of yeast mash thereto, the main fermentation was carried out at 20° C. for 10 days. After removing the pericarp and sediments by pressing, the fermented liquor was transferred into a barrel provided with a fermentation bung and subjected to the after-fermentation at 15° C. Then it was stored and aged for 2 years while separating the sediments (tartar, tannin, protein, etc.)

Reference Example 3

Method for Purifying Procyanidin B-2 (epicatechin-(4β→8)-epicatechin) from an Apple Juice An apple juice (21,120 kg) was passed through a column (diameter: 60 cm, length: 88.5 cm, 250 l in volume) packed with Diaion HP-20 Resin (manufactured by Mitsubishi Chemical Industries, Ltd.) which had been equilibrated with water. Then, the column was washed with 1,000 l of a desalted water and 500 l of a 15% (V/V) aqueous methanol solution. Subsequently, the aimed product was eluted with 500 l of a 45% (V/V) aqueous methanol solution. The eluate was solidified by drying and thus 9,450 g of a dry solid matter was obtained.

This dry solid matter (1,465 g) was dissolved in a 25% (V/V) aqueous methanol solution and the solution was passed through a column (diameter: 18 cm, length: 39.3 cm, 10 l in volume) packed with Sephadex LH-20 (manufactured by Pharmacia) which had been equilibrated with a 25% (V/V) aqueous methanol solution. Next, the column was washed successively with 20 l of a 25% (V/V) aqueous methanol solution and 20 l of a 50% (V/V) aqueous methanol solution and then the aimed product was eluted with 20 l of a 75% (V/V) aqueous methanol solution. The eluate was solidified by drying to give 233 g of a dry solid matter.

This dry solid matter (116 g) was dissolved in a desalted water and separated by preparative high-performance liquid chromatography (150 mmΦ×1000 mm: ODS column, methanol/a 0.0001% aqueous acetic acid solution =12/88). Thus, 16.5 g of procyanidin B-2 (purity: 94% or more) was obtained. The $^1$H-NMR and $^{13}$C-NMR spectra and mass spectrum of the procyanidin B-2 thus obtained agreed with the spectra of a specimen. The purity of procyanidin B-2 was analyzed by HPLC under the same conditions as in Test Example 2.

Reference Example 4

Purification of Proanthocyanidin from Grape Seeds

Proanthocyanidin was extracted and purified from grape (chardonnay) seeds by the method described in Acta Derm. Venereol. (Stockh.) 78, 428 (1998) to give a grape seed-origin proanthocyanidin having an average degree of polymerization of 3.5 and a galloylation ratio of 25% by mol per monomer constituting proanthocyanidin.

The galloylation ratio and average degree of polymerization were determined in accordance with the method described in Acta Derm. Venereol. (Stockh.), 78, 428 (1998).

According to the invention, proanthocyanidin-containing compositions excellent in proanthocyanidin stability, drinks, foods, cosmetics and medicaments containing these compositions, and a method for stabilizing proanthocyanidin to prevent its color change, etc. caused by oxidative polymerization and the like are provided.

While the invention has been described in detail and with reference to specific embodiments thereof, it will be apparent to one skilled in the art that various changes and modifications can be made therein without departing from the spirit and scope thereof.

This application is based on Japanese patent application No. Hei.-11-266430 filed on Sep. 21, 1999, herein incorporated by reference.

What is claimed is:

1. A composition containing proanthocyanidin obtained from a fruit of a plant belonging to the genus Malus, and a vitamin $B_6$ derivative or a salt thereof.

2. The composition as claimed in claim 1, wherein the concentration of said vitamin $B_6$ derivative or the salt thereof ranges from 0.001 to 1% by weight based on the total weight of the composition.

3. The composition as claimed in claim 1, wherein the concentration of proanthocyanidin ranges from 0.01 to 20% by weight based on the total weight of the composition.

4. The composition as claimed in claim 1, wherein the concentration of said vitamin $B_6$ derivative or the salt thereof ranges from 0.001 to 1% by weight based on the total weight of the composition and the concentration of proanthocyanidin ranges from 0.01 to 20% by weight based on the total weight of the composition.

5. The composition as claimed in any of claims 1 to 4, wherein said vitamin $B_6$ derivative is selected from the group consisting of pyridoxine, pyridoxal, pyridoxamine and phosphates thereof.

6. A drink containing the composition as claimed in any of claims 1 to 4.

7. The drink as claimed in claim 6, which is selected from the group consisting of a fruit liquor, a fruit drink and a health drink.

8. A food containing the composition as claimed in any of claims 1 to 4.

9. A cosmetic containing the composition as claimed in any of claims 1 to 4.

10. A medicament containing the composition as claimed in any of claims 1 to 4.

11. A method of stabilizing proanthocyanidin comprising the steps of:

selecting a proanthocyanidin obtained from a fruit of a plant belonging to the genus Malus; and blending said proanthocyanidin with a vitamin $B_6$ derivative or a salt thereof.

12. The composition as claimed in claim 1, wherein said proanthocyanidin is an extract containing proanthocyanidin obtained from a fruit of a plant belonging to its genus Malus.

13. The composition as claimed in claim 12, wherein said extract was extracted using a solvent.

14. The composition as claimed in claim 13, wherein the solvent is at least one solvent selected from the group consisting of water, alcohols, ketones and esters.

15. The composition as claimed in claim 13, wherein the solvent is at least one solvent selected from the group consisting of water, ethanol, methanol, isopropyl alcohol, acetone, methyl ethyl ketone, methyl acetate and ethyl acetate.

* * * * *